(12) United States Patent
Raab et al.

(10) Patent No.: US 9,802,004 B2
(45) Date of Patent: Oct. 31, 2017

(54) DRIVE MECHANISM FOR A MEDICATION DELIVERY DEVICE AND MEDICATION DELIVERY DEVICE

(75) Inventors: Steffen Raab, Frankfurt am Main (DE); Sandra Arnhold, Büttelborn (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1155 days.

(21) Appl. No.: 13/393,331

(22) PCT Filed: Sep. 3, 2010

(86) PCT No.: PCT/EP2010/062924
§ 371 (c)(1),
(2), (4) Date: Aug. 3, 2012

(87) PCT Pub. No.: WO2011/026928
PCT Pub. Date: Mar. 10, 2011

(65) Prior Publication Data
US 2012/0296286 A1   Nov. 22, 2012

(30) Foreign Application Priority Data

Sep. 7, 2009  (EP) .................................... 09011420

(51) Int. Cl.
*A61M 5/315* (2006.01)
*A61M 5/24* (2006.01)

(52) U.S. Cl.
CPC .... *A61M 5/31593* (2013.01); *A61M 5/31551* (2013.01); *A61M 5/31583* (2013.01); *A61M 5/24* (2013.01)

(58) Field of Classification Search
CPC ........ A61M 5/20; A61M 5/315; A61M 5/286; A61M 5/282; A61M 5/2425;
(Continued)

(56) References Cited

U.S. PATENT DOCUMENTS 533,575 A      2/1895  Wilkens
3,790,048 A *  2/1974  Luciano et al. .............. 222/390
(Continued)

FOREIGN PATENT DOCUMENTS

DE       10237258       3/2004
DE    102007052013      5/2009
(Continued)

OTHER PUBLICATIONS

International Preliminary Report on Patentability and Written Opinion for Int. App. No. PCT/EP2010/062924, dated Mar. 22, 2012.
(Continued)

*Primary Examiner* — Imani Hayman
*Assistant Examiner* — Matthew A Engel
(74) *Attorney, Agent, or Firm* — McDonnell Boehnen Hulbert & Berghoff LLP

(57) ABSTRACT

A piston rod is arranged in a body and provided with a helical element and an axial element. A guide element, which is arranged in the body and fixed relatively to the body, is coupled to the helical element to guide a helical movement of the piston rod and coupled to the axial element to guide an axial movement of the piston rod. The axial movement allows a priming of the device preceding the helical movement of the piston rod.

18 Claims, 4 Drawing Sheets

(58) Field of Classification Search
CPC ............ A61M 5/2429; A61M 5/31586; A61M 5/3272; A61M 5/31585; A61M 5/31543
See application file for complete search history.

(56) References Cited

U.S. PATENT DOCUMENTS

| | | | | |
|---|---|---|---|---|
| 4,973,318 | A * | 11/1990 | Holm et al. | 604/208 |
| 5,112,317 | A * | 5/1992 | Michel | 604/208 |
| 5,226,895 | A | 7/1993 | Harris | |
| 5,279,585 | A * | 1/1994 | Balkwill | 604/207 |
| 5,279,586 | A | 1/1994 | Balkwill | |
| 5,304,152 | A | 4/1994 | Sams | |
| 5,320,609 | A | 6/1994 | Haber et al. | |
| 5,383,865 | A | 1/1995 | Michel | |
| 5,480,387 | A | 1/1996 | Gabriel et al. | |
| 5,505,704 | A | 4/1996 | Pawelka et al. | |
| 5,545,147 | A * | 8/1996 | Harris | 604/209 |
| 5,582,598 | A | 12/1996 | Chanoch | |
| 5,626,566 | A | 5/1997 | Petersen et al. | |
| 5,643,214 | A * | 7/1997 | Marshall et al. | 604/134 |
| 5,674,204 | A | 10/1997 | Chanoch | |
| 5,688,251 | A | 11/1997 | Chanoch | |
| 5,713,857 | A * | 2/1998 | Grimard et al. | 604/82 |
| 5,851,197 | A * | 12/1998 | Marano et al. | 604/135 |
| 5,921,966 | A | 7/1999 | Bendek et al. | |
| 5,961,495 | A | 10/1999 | Walters et al. | |
| 6,004,297 | A | 12/1999 | Steenfeldt-Jensen et al. | |
| 6,068,614 | A * | 5/2000 | Kimber et al. | 604/200 |
| 6,193,698 | B1 | 2/2001 | Kirchhofer et al. | |
| 6,221,046 | B1 | 4/2001 | Burroughs et al. | |
| 6,235,004 | B1 | 5/2001 | Steenfeldt-Jensen et al. | |
| 6,248,095 | B1 | 6/2001 | Giambattista et al. | |
| 6,899,698 | B2 | 5/2005 | Sams | |
| 6,936,032 | B1 | 8/2005 | Bush, Jr. et al. | |
| 7,094,221 | B2 * | 8/2006 | Veasey et al. | 604/187 |
| 7,241,278 | B2 * | 7/2007 | Moller | 604/211 |
| 7,427,275 | B2 * | 9/2008 | DeRuntz et al. | 604/207 |
| 7,481,977 | B2 * | 1/2009 | Percival et al. | 422/64 |
| 7,850,662 | B2 * | 12/2010 | Veasey et al. | 604/207 |
| 7,918,833 | B2 * | 4/2011 | Veasey et al. | 604/209 |
| 7,935,088 | B2 * | 5/2011 | Veasey et al. | 604/207 |
| 7,985,201 | B2 * | 7/2011 | Langley et al. | 604/131 |
| 8,257,319 | B2 * | 9/2012 | Plumptre | 604/211 |
| 2002/0052578 | A1 | 5/2002 | Moller | |
| 2002/0120235 | A1 | 8/2002 | Enggaard | |
| 2003/0050609 | A1 | 3/2003 | Sams | |
| 2004/0059299 | A1 | 3/2004 | Moller | |
| 2004/0210199 | A1 * | 10/2004 | Atterbury et al. | 604/224 |
| 2004/0249348 | A1 * | 12/2004 | Wimpenny et al. | 604/207 |
| 2004/0260247 | A1 * | 12/2004 | Veasey et al. | 604/207 |
| 2004/0267207 | A1 | 12/2004 | Veasey et al. | |
| 2005/0033244 | A1 * | 2/2005 | Veasey et al. | 604/211 |
| 2005/0113765 | A1 | 5/2005 | Veasey et al. | |
| 2006/0153693 | A1 | 7/2006 | Fiechter et al. | |
| 2006/0264839 | A1 * | 11/2006 | Veasey et al. | 604/209 |
| 2008/0027397 | A1 * | 1/2008 | DeRuntz et al. | 604/220 |
| 2009/0198193 | A1 * | 8/2009 | Veasey et al. | 604/207 |
| 2009/0264828 | A1 * | 10/2009 | Dette et al. | 604/189 |
| 2009/0275916 | A1 | 11/2009 | Harms et al. | |
| 2010/0094205 | A1 * | 4/2010 | Boyd et al. | 604/68 |
| 2010/0094206 | A1 * | 4/2010 | Boyd et al. | 604/68 |
| 2010/0094207 | A1 * | 4/2010 | Boyd et al. | 604/68 |
| 2010/0094253 | A1 * | 4/2010 | Boyd et al. | 604/506 |
| 2010/0137792 | A1 * | 6/2010 | Boyd et al. | 604/68 |
| 2010/0324494 | A1 * | 12/2010 | Plumptre | 604/207 |
| 2010/0324496 | A1 * | 12/2010 | Plumptre et al. | 604/207 |
| 2010/0324497 | A1 * | 12/2010 | Plumptre | 604/207 |
| 2010/0324527 | A1 * | 12/2010 | Plumptre | 604/500 |
| 2010/0331788 | A1 * | 12/2010 | Plumptre et al. | 604/207 |
| 2010/0331790 | A1 * | 12/2010 | Plumptre | 604/207 |
| 2010/0331791 | A1 * | 12/2010 | Plumptre | 604/207 |
| 2010/0331792 | A1 * | 12/2010 | Plumptre | 604/207 |
| 2010/0331806 | A1 * | 12/2010 | Plumptre et al. | 604/500 |
| 2011/0152784 | A1 * | 6/2011 | Veasey et al. | 604/207 |
| 2012/0010575 | A1 * | 1/2012 | Jones et al. | 604/211 |
| 2012/0022462 | A1 * | 1/2012 | Plumptre | 604/197 |
| 2012/0046643 | A1 * | 2/2012 | Plumptre et al. | 604/506 |
| 2012/0089098 | A1 * | 4/2012 | Boyd et al. | 604/189 |
| 2012/0089100 | A1 * | 4/2012 | Veasey et al. | 604/209 |
| 2012/0283652 | A1 * | 11/2012 | MacDonald et al. | 604/211 |
| 2012/0283654 | A1 * | 11/2012 | MacDonald et al. | 604/211 |
| 2012/0283658 | A1 * | 11/2012 | Plumptre et al. | 604/211 |
| 2012/0283662 | A1 * | 11/2012 | MacDonald et al. | 604/236 |
| 2013/0030409 | A1 * | 1/2013 | Macdonald et al. | 604/506 |

FOREIGN PATENT DOCUMENTS

| | | |
|---|---|---|
| EP | 0937471 | 8/1999 |
| EP | 0937476 | 8/1999 |
| EP | 1003581 B1 | 11/2000 |
| WO | 99/38554 | 8/1999 |
| WO | 01/10484 | 2/2001 |
| WO | 2004/016307 | 2/2004 |
| WO | 2004/078242 | 9/2004 |
| WO | 2008/138908 A1 | 11/2008 |
| WO | 2008/148540 A1 | 12/2008 |

OTHER PUBLICATIONS

International Search Report for International App. No. PCT/EP2010/062924, dated Nov. 3, 2010.

* cited by examiner

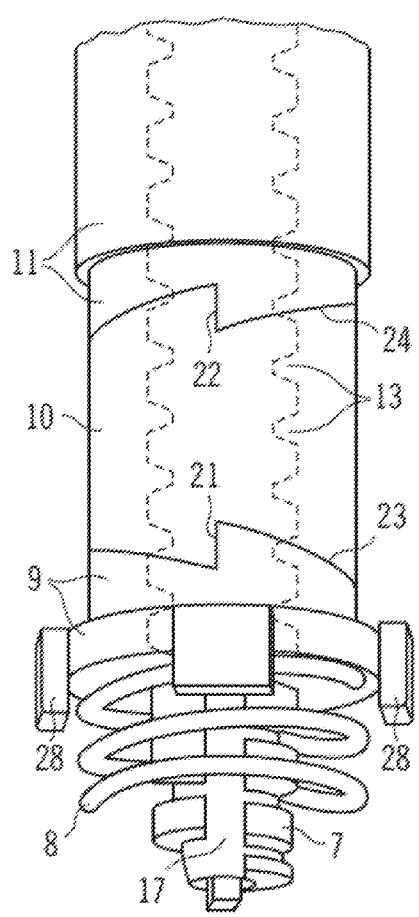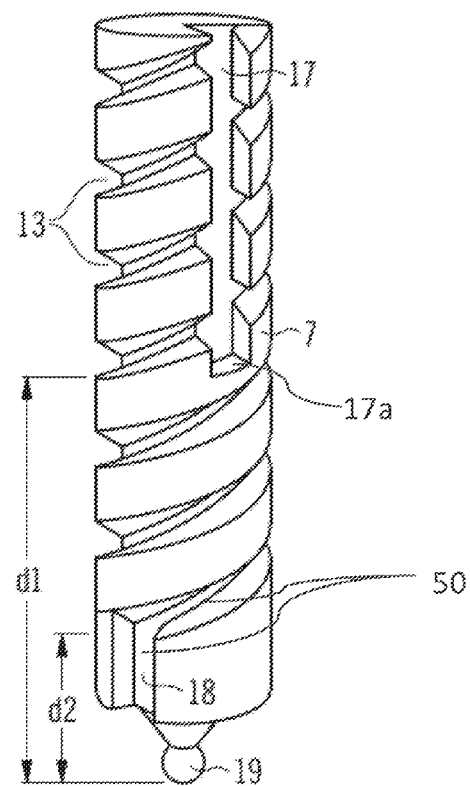

DRIVE MECHANISM FOR A MEDICATION DELIVERY DEVICE AND MEDICATION DELIVERY DEVICE

CROSS REFERENCE TO RELATED APPLICATIONS

The present application is a U.S. National Phase Application pursuant to 35 U.S.C. §371 of International Application No. PCT/EP2010/062924 filed Sep. 3, 2010, which claims priority to European Patent Application No. 09011420.8 filed on Sep. 7, 2009. The entire disclosure contents of these applications are herewith incorporated by reference into the present application.

FIELD OF INVENTION

The present invention relates to a drive mechanism for a medication delivery device and a medication delivery device incorporating such a drive mechanism.

BACKGROUND

Portable medication delivery devices are generally known for the administration of a medicinal fluid or drug that is suitable for the self-administration by a patient. A drug injection device is especially useful in the shape of a pen, which can be handled easily and kept everywhere available. A sophisticated type of drug delivery device is constructed to be refillable and reusable many times. A dose of a drug is delivered by means of a drive mechanism, which also allows to set the amount of fluid to be thus injected.

DE 102 37 258 B4 describes a drug delivery device in the shape of an injection pen having a drive mechanism, which allows to deliver a plurality of different prescribed doses. The drive mechanism comprises rotatable elements, which are rotated relatively to one another around a common axis and are coupled by a gear that is arranged between opposite faces of the rotatable elements. The gear comprises a modified ratchet formed by sequences of corresponding ramps sloping in azimuthal direction along the rims of the opposite faces of the rotatable elements. The slope of each ramp is followed by a steep flank, thus rendering a sawtooth shape of the gear, which is apparent when the rotatable elements are viewed during rotation in a radial direction towards the axis.

SUMMARY

It is an object of the present invention to disclose an improved drive mechanism for a medication delivery device that allows a priming.

This object is achieved by a drive mechanism according to claim 1. Variants and embodiments can be derived from the dependent claims.

The drive mechanism for a medication delivery device is arranged in a body or housing that has a proximal end and a distal end. A piston rod, which is to be driven by the drive mechanism, is arranged within the body along an axis of rotation. A drive member is arranged within the body and is rotationally coupled with the piston rod with respect to the axis of rotation. The piston rod is helically movable with respect to the body, the movement comprising a rotation around the axis and a simultaneous shift along the axis. The piston rod is provided with a guide track comprising a helical element and an axial element. A guide element is arranged within the body and is fixed relatively to the body. The guide element is coupled to the guide track of the piston rod. When the guide element is coupled to the helical element, the guide element guides the helical movement of the piston rod, and when the guide element is coupled to the axial element, it guides an axial movement of the piston rod in the direction to the distal end of the body, the axial movement preceding the helical movement.

The body can be designed to house, fix or protect components of a medication delivery device (particularly the drive mechanism and the piston rod), preferably by limiting the exposure to contaminants such as liquids, dust or dirt. The body can be unitary or a multipart component of tubular or non-tubular shape.

The term "distal end" refers to a part of the body which is intended to be arranged at a portion of the medication delivery device from which a medication is dispensed. The term "proximal end" refers to a part of the body which is remote from the distal end.

The term "piston rod" encompasses any element that is provided to transfer a movement to the piston, especially for the purpose of dispensing a drug or medicament. The piston rod may be flexible or not. It may be of unitary or multipart construction, and may especially be a simple rod, a lead-screw, a rack-and-pinion, a worm gear system, or the like.

In an embodiment of the drive mechanism, the piston rod has a distal end, which is nearest to the distal end of the body and engages a piston or a bearing that is arranged between the piston and the piston rod to reduce damages that may be caused by friction. The piston is provided to expel a medicament from a reservoir or an ampoule.

In an embodiment of the drive mechanism, the helical element of the piston rod is a screw thread, and the helical movement of the piston rod is caused by the screw thread. The guide element, which is fixed with respect to the body, slides along the screw thread of the piston rod and thus guides the helical movement of the piston rod. The guide element can be a lug or spike sticking out from an inner wall of the body, for example.

In a further embodiment, the axial element of the piston rod is an axial groove leading into the screw thread.

In a further embodiment, the rotation of the piston rod is effected by a drive member, which is rotationally coupled with the piston rod by means of an axial groove or track of the piston rod, the axial groove having a limit in the direction of the distal end.

In a further embodiment, the drive member is arranged in such a manner that it can be shifted towards the distal end. The drive member is coupled with the piston rod by means of an axial thread engaging the axial groove of the piston rod. The drive member shifts the piston rod towards the distal end when the drive member is shifted towards the distal end while the axial thread is in contact with the limit of the axial groove and the guide element is coupled to the axial element of the piston rod. The piston rod can be provided to be shifted towards the distal end by the drive member in a priming step.

In a further embodiment, the axial groove intersects the screw thread and allows an axial movement of the piston rod with respect to the drive member. The axial groove ends at a first distance from the distal end of the piston rod. The screw thread of the piston rod likewise ends at a second distance from the distal end of the piston rod and leads into a further axial groove, which extends to the distal end of the piston rod. The first distance is larger than the second distance, so that the further axial groove is shorter than the first distance between the end of the piston rod and the end of the axial groove provided for rotating the piston rod.

The further axial groove enables an axial movement of the piston rod without rotation as long as the piston rod is near a position in which it is closest to the proximal end of the body. An axial shift of the piston rod from this position towards the distal end of the body takes place without rotation of the piston rod until the guide element of the body has completely passed the further axial groove and engages the screw thread of the piston rod. Then the helical movement of the piston rod with respect to the body commences. In a priming step, the distal limit of the axial groove that is coupled with the drive member is used to shift the piston rod towards the distal end of the body. This causes the guide element to attain the beginning of the screw thread of the piston rod and thus the piston rod to occupy a well-defined position with respect to the body and with respect to a receptacle in the body containing the drug or medicament to be delivered. The first dose is therefore delivered precisely as it was set, because an accidental movement of the piston is prevented by the exact initial positioning of the piston rod.

In an embodiment of the drive mechanism, a dose member is provided to set each dose that is to be delivered, and the priming of the piston rod is performed by pushing the dose member towards the distal end of the body. The dose member can be a dose sleeve, which is coupled with the piston rod in such a manner as to allow the piston rod to be shifted towards the distal end by means of the dose sleeve.

In a further embodiment, the piston rod is shifted towards the distal end by means of the dose member while the guide element is coupled to the axial element of the piston rod. The piston rod can be provided to be shifted towards the distal end by the dose member in a priming step.

In a further embodiment, a stop member is arranged within the body and rotationally coupled with the body. This means that a rotation of the stop member with respect to the body is inhibited. A spring is arranged within the body, the spring exerting a force on the stop member in the direction to the proximal end. A drive member is arranged within the body on the side of the stop member facing the proximal end. The drive member is rotationally coupled with the piston rod and movable relatively to the piston rod along the axis. A drive sleeve is arranged within the body on the side of the drive member facing the proximal end. The drive sleeve is rotatable with respect to the body around the axis. A gear couples the drive member and the stop member rotationally when the drive sleeve is rotated in a first sense of rotation around the axis. A further gear couples the drive member and the drive sleeve rotationally when the drive sleeve is rotated in a second sense of rotation, which is opposite to the first sense of rotation, around the axis. A dose sleeve is arranged within the body and is helically movable with respect to the body, the movement comprising a rotation around the axis and a simultaneous shift along the axis. The dose sleeve and the drive sleeve are coupled, the coupling producing a rotation of the drive sleeve in the second sense of rotation around the axis when the dose sleeve is moved towards the distal end.

A further embodiment of the drive mechanism comprises a means guiding the piston rod in such a manner that the helical movement of the piston rod advances the piston rod towards the distal end when the piston rod is rotated in the second sense of rotation with respect to the body.

In a further embodiment, a piston, movable by the piston rod, can be arranged in a receptacle at the distal end within the body. The receptacle may especially be provided for a cartridge, and the piston may be inserted in the cartridge.

In a further embodiment of the drive mechanism, a dose is set by a movement of the dose sleeve in the direction to the proximal end, and a medication is delivered by a movement of the dose sleeve in the direction to the distal end.

In a further embodiment of the drive mechanism, it is part of a medication delivery device. The body can have the shape of an injection pen, for instance.

In a further embodiment, the medication delivery device comprises a receptacle at the distal end within the body and a piston within the receptacle, the piston being movable along the axis by means of the piston rod. The receptacle can be provided for a cartridge, and the piston can be inserted in the cartridge.

In a further embodiment of the medication delivery device, a dose is set by a movement of a dose sleeve in the direction to the proximal end, and a medication is delivered by a movement of the dose sleeve in the direction to the distal end.

These and other features of the invention will become apparent from the following brief description of the drawings, detailed description and appended claims and drawings.

BRIEF DESCRIPTION OF THE FIGURES

FIG. 3 shows a detailed view of a part of an embodiment of the drive mechanism comprising a stop member, a drive member, and a drive sleeve.

FIG. 4 shows a perspective view of a portion of the piston rod including its distal end.

DETAILED DESCRIPTION

Figure 1:
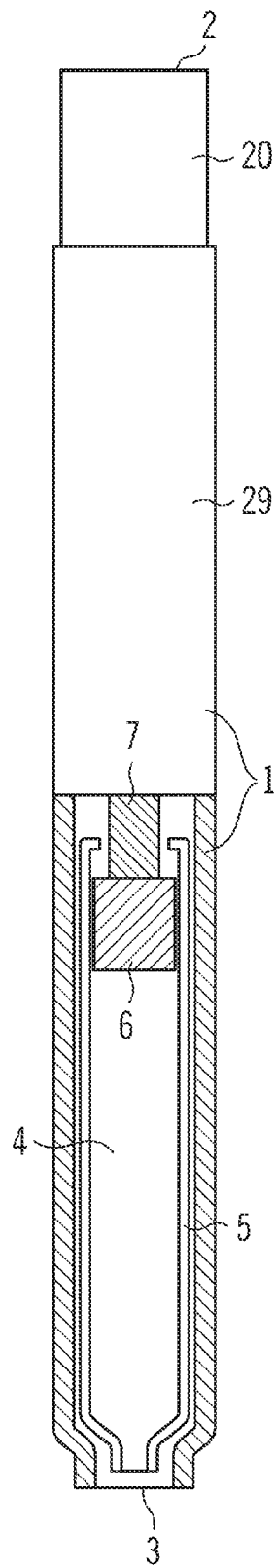
FIG. 1 shows a schematic cross-section of a medication delivery device in the shape of an injection pen.

Similar or corresponding elements of different embodiments are designated with the same reference numerals in the figures.

FIG. 1 shows a schematic cross-section of a medication delivery device in the shape of an injection pen. The medication delivery device can have other suitable shapes instead. The device comprises a housing or body 1. The term "body" encompasses any exterior housing, like a main housing or shell, as well as an interior housing, like an insert or inner body arranged within an exterior housing.

In the embodiment shown in FIG. 1, the body 1 is of elongated shape. It has a proximal end 2 and a distal end 3. The body 1 can be composed of at least two attachable and separable parts enabling a refill of the device. The body 1 comprises a receptacle 4 provided for a drug or medicament. The receptacle 4 can be designed to be filled by means of a cartridge 5 containing the drug and being inserted in the receptacle 4. When the cartridge 5 is empty, it can be removed and substituted with a new cartridge. The drug is dispensed through an opening of the receptacle by means of a piston 6, which is advanced in the receptacle, particularly within the cartridge 5, towards the distal end 3 by means of a piston rod 7 to expel the drug.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an antibody, an enzyme, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The distal end 3 can be provided with a needle, not shown in FIG. 1, or with a needle unit, for instance. If the piston rod 7 is to be moved relatively to the piston 6, a bearing, not shown in FIG. 1, can be arranged between the piston 6 and the piston rod 7 to reduce damages that may be caused by friction. FIG. 1 indicates the location 29 of a drive mechanism, which may be operated by a dose button 20 at the proximal end 2.

The drug or medicament used in conjunction with the device shown in FIG. 1 is preferably a liquid medication. A full cartridge 5 preferably contains a plurality of doses of the medication, which can be insulin, heparin, or growth hormones, for example. The device may be disposable or reusable, and it may be configured to dispense fixed doses of the medication or variable doses. The drug may be administered by a needle, or the device may be needle-free.

Figure 2:
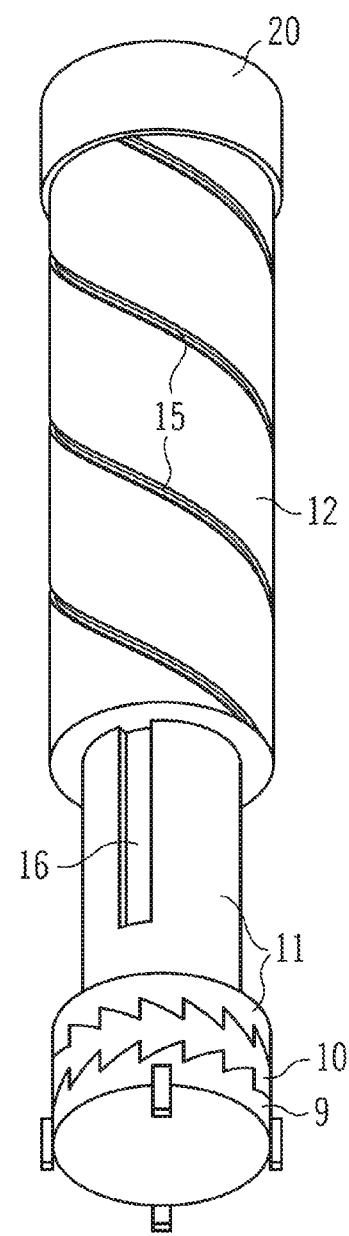
FIG. 2 shows a perspective view of a part of a drive mechanism.

FIG. 2 shows a perspective view of a part of an embodiment of the drive mechanism. A stop member 9, a drive member 10 and a drive sleeve 11 are engaged by a ratchet coupling the drive member 10 and the stop member 9 and by a ratchet coupling the drive member 10 and the drive sleeve 11. The ratchets and their function will be described in more detail below. The drive sleeve 11 is arranged within a dose sleeve 12, which is provided with a screw thread 15. The drive sleeve 11 and the dose sleeve 12 are rotationally coupled, which may be effected by an axial groove 16 of the drive sleeve 11, for example. The drive sleeve 11 can be moved axially with respect to the dose sleeve 12, but not rotated with respect to the dose sleeve 12. The dose sleeve 12 is provided with the dose button 20.

The dose sleeve 12 is movable with respect to the body 1. A movement of the dose sleeve 12 in the proximal direction sets a dose of the medication which is to be delivered and a movement of the dose sleeve 12 in the distal direction effects a delivery of the set dose. The dose sleeve 12 is guided by the screw thread 15 on a helical movement with respect to the body 1, which can be provided with a corresponding thread. The thread engaging the thread 15 of the dose sleeve 12 can instead be provided on a further component that is fixed with respect to the body 1. Proximal and distal end positions of the movement of the dose sleeve 12 may be determined by respective stop features provided at the body 1.

The drive member 10 is rotatable with respect to the body 1 and configured to transfer a rotation to the piston rod 7. The drive member 10 engages the piston rod 7 by means of a rotational coupling. The stop member 9 is rotationally coupled to the body 1. This is explained in more detail below.

During the setting of a dose, the dose sleeve 12 and, because of the rotational coupling, the drive sleeve 11 are rotated with respect to the body 1 in a first sense of rotation. A rotation of the drive member 10 with respect to the body 1 in the first sense of rotation is inhibited by the gear between the drive member 10 and the stop member 9, because this gear rotationally couples the stop member 9 and the drive member 10 in the first sense of rotation. If the drive sleeve 11 rotates with respect to the body 1 in an opposite second sense of rotation, the gear between the drive member 10 and the drive sleeve 11 rotationally couples the drive member 10 and the drive sleeve 11, so that the drive member 10 is rotated in the same sense of rotation and with the same angular velocity as the drive sleeve 11. In this second sense of rotation, which is to take place during a delivery of the medicament, the rotation is therefore transferred from the drive member 10 to the piston rod 7.

FIG. 3 shows the gears between the stop member 9, the drive member 10 and the drive sleeve 11. The drive sleeve 11 is coupled to the drive member 10 by a uni-directional gear, which permits a rotation of the drive sleeve 11 with respect to the drive member 10 when the drive sleeve 11 rotates in the first sense of rotation with respect to the body 1. The gear prevents a rotation of the drive sleeve 11 with respect to the drive member 10, when the drive sleeve 11 rotates in the second sense of rotation with respect to the body 1. The drive member 10 thus follows a rotation of the drive sleeve 11 in the second sense of rotation during a delivery of a medicament. In the embodiment shown in FIG. 3, the gears form a kind of ratchet.

The drive member 10 comprises teeth disposed azimuthally along the perimeter of the components and forming a kind of ratchet 21 coupling the drive member 10 and the stop member 9 and a kind of ratchet 22 coupling the drive member 10 and the drive sleeve 11. Ramps 23 of the ratchet 21 coupling the drive member 10 and the stop member 9 and ramps 24 of the ratchet 22 coupling the drive member 10 and the drive sleeve 11 are arranged in such a fashion that a relative rotation of those two components that abut at one of the gears is possible in one sense of rotation while the relative rotation of the two components is inhibited in the opposite sense of rotation. Thus the rotational coupling described above is achieved. The stop member 9 can be provided with protruding parts like the teeth 28 shown in FIG. 3 to allow a rotational coupling of the stop member 9 with the body 1. If the teeth 28 are guided in axial grooves in the body 1, the stop member 9 can be moved axially, but not rotated with respect to the body 1. This clearly shows that a rotation of the drive sleeve 11 in the second sense of rotation, thus engaging the ratchet 22 between the drive sleeve 11 and the drive member 10, produces a rotation of the drive member 10 relatively to the rotationally fixed stop member 9, whereas rotating the drive sleeve 11 in the first sense of rotation during an engagement of the ratchet 21 between the drive member 10 and the stop member 9 produces a rotation of the drive sleeve 11 relatively to the drive member 10, because the drive member 10 cannot rotate in the first sense of rotation because of its coupling to the rotationally fixed stop member 9. During the setting of a dose the drive member 10 therefore does not rotate, and during a delivery of a dose the drive member 10 rotates to generate a simultaneous rotation of the piston rod 7 according to the further mechanism that will be described in conjunction with FIGS. 7 and 8.

FIG. 4 shows a perspective view of a portion of the piston rod 7 including its distal end 19. The piston rod 7 comprises a screw thread 13 and an axial groove 17 intersecting the screw thread 13 in the longitudinal direction of the piston rod 7. Although the screw thread 13 is thus periodically interrupted within each turn of the screw thread 13, its function to guide the helical movement of the piston rod 7, when it approaches the distal end 3 of the body 1 during the delivery of the medicament, is not inhibited by the axial groove 17. FIG. 4 clearly shows that the axial groove 17 ends at a first distance d1 from the distal end 19 of the piston rod 7. The axial groove 17 thus enables a protruding element of the drive member 10 to couple the drive member 10 rotationally with the piston rod 7, at the same time allowing an axial movement of the drive member 10 with respect to the piston rod 7. The axial movement of the drive member 10 with respect to the piston rod 7 is stopped when the protruding element of the drive member 10 hits the stop or limit 17a at the end of the axial groove 17. If the axial movement of the drive member 10 with respect to the body 1 is continued by the operation of the mechanism, the drive member 10 shifts the piston rod 7 in the direction to the distal end 3 of the body 1.

Figure 6:
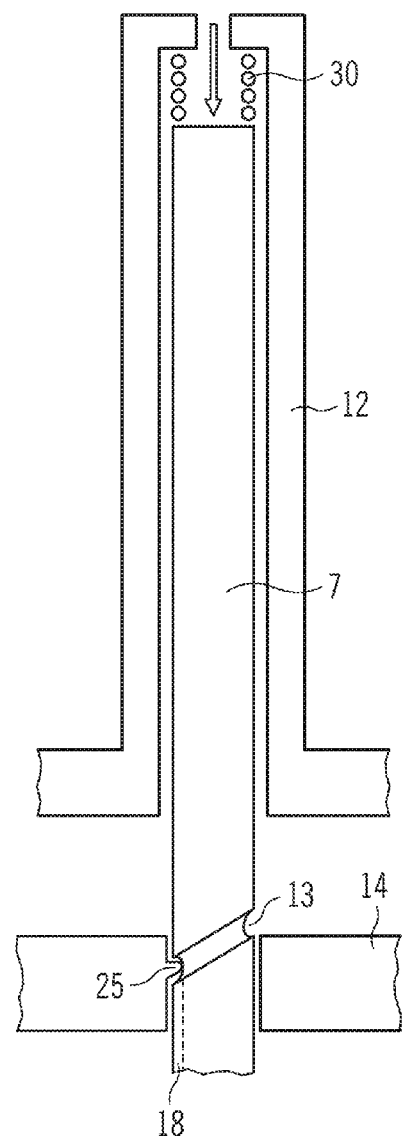
FIG. 6 shows a schematic cross-section of a further embodiment of the drive mechanism.

At the distal end 19 of the piston rod 7 the helical turns of the screw thread 13, i.e., the helical element of guide track 50, end in a further axial groove 18, i.e., the axial element of guide track 50. A guide element 25 of the body 1, as illustrated in FIG. 6, that is provided to slide in the guide track 50 so that the guide element 25 slides and travels in screw thread 13 of the piston rod 7 to generate helical movement of the piston rod with respect to the body 1 and the guide element 25 does not generate a rotation of the piston rod 7 with respect to the body 1 as long as the guide element stays in the further axial groove 18 of guide track 50. The piston rod 7 can therefore be moved axially without rotation towards the distal end 3 of the body 1 until the guide element hits the first turn of the screw thread 13 at a second distance d2 from the distal end 19 of the piston rod 7. At this position the axial movement of the piston rod 7 is stopped, and the helical movement of the piston rod 7 commences when the piston rod 7 is rotated by means of the drive member 10.

Figure 5:
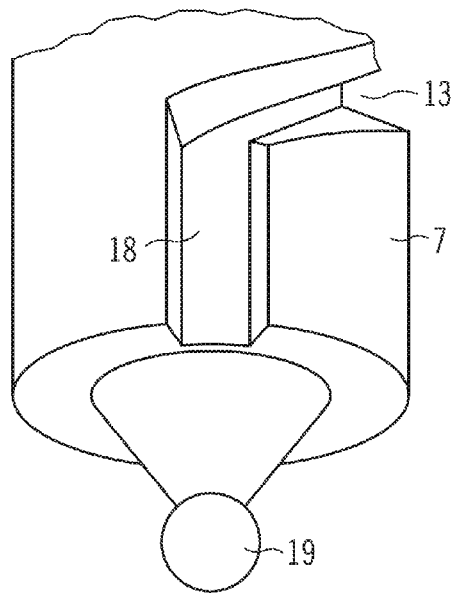
FIG. 5 shows an enlarged perspective view of the distal end of the piston rod.

FIG. 5 shows an enlarged perspective view onto the distal end 19 of the piston rod 7. It shows how the further axial groove 18 leads into the screw thread 13.

FIG. 6 shows a schematic cross-section of a further embodiment of the drive mechanism. In this embodiment, the dose member 12 is directly used to shift the piston rod 7 towards the distal end 3 during the priming step by means of a spring 30 exerting a force onto the piston rod 7 in the direction of the arrow. An internal interface 14 of the body 1 is used to guide the piston rod 7 and to generate its helical movement. This is effected by a guiding element 25 of the internal interface 14. The guiding element slides in the screw thread 13 of the piston rod 7. Only the first turn of the screw thread 13 is shown in the schematic cross section of FIG. 6. The further axial groove 18 is indicated by the broken line of its hidden contour. The cross-section of FIG. 6 clearly shows that the piston rod 7 can be shifted in the direction of the arrow without rotation until the guide element 25 reaches the first turn of the screw thread 13 and the priming 16 step is complete. The further movement of the piston rod 7 is helical with respect to the body 1 and is generated by a rotation of the piston rod 7.

Figure 7:
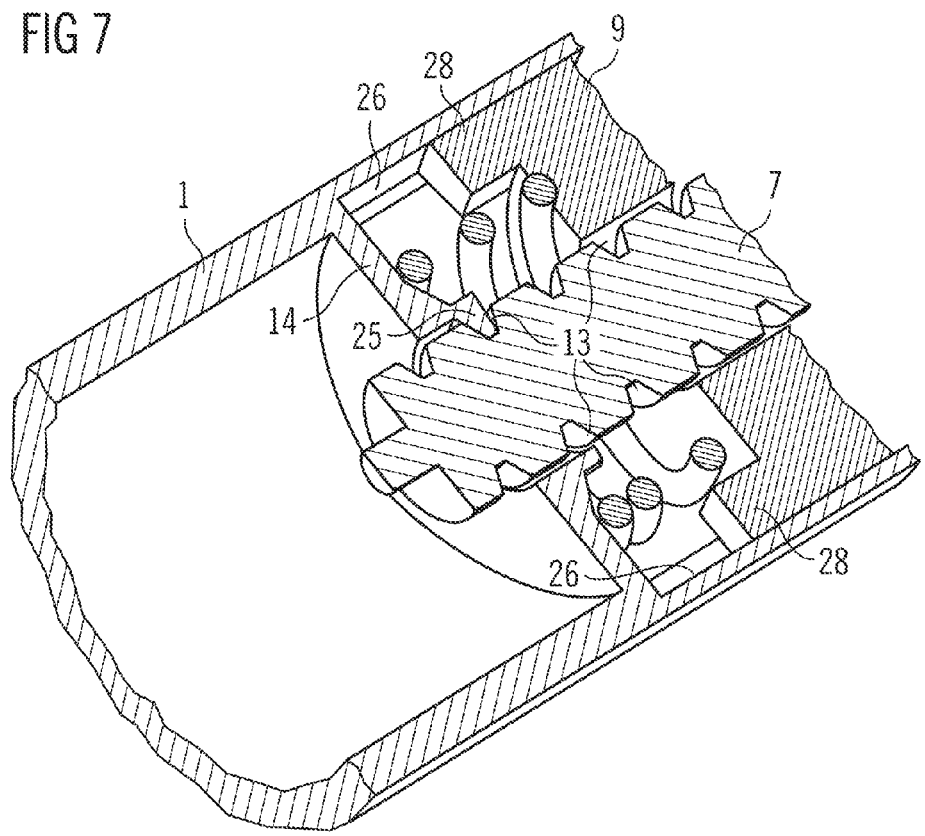
FIG. 7 shows a cross-section of a part of an embodiment of the drive mechanism comprising a body, a piston rod, and a means guiding the piston rod in a helical movement.

FIG. 7 shows a cross-section of a part of an embodiment of the drive mechanism having means for guiding the piston rod 7 in a helical movement with respect to the body 1. The drive mechanism comprises a spring 8. The spring 8 is provided to maintain the stop member 9 in contact with drive member 10 during an operation of the drive mechanism. FIG. 7 shows a possible arrangement of the spring 8 between the stop member 9 and a support member, which is an internal interface 14 of the body 1 in the embodiment shown in FIG. 7. The internal interface 14 can be provided with an opening having a guide element 25, by which the piston rod 7 is guided. To this end, the piston rod 7 is provided with a screw thread 13, which generates a helical movement of the piston rod 7 with respect to the body 1, when the piston rod 7 is moved through the opening of the internal interface 14 and the guiding element 25 slides through the screw thread 13.

The stop member 9 is shown to have teeth 28, which are guided within axial guides 26 formed in an inner wall of the body 1. This is an example of a rotational coupling between the stop member 9 and the body 1, which enables an axial relative movement.

If the stop member 9 is shifted in the direction of the distal end, the spring 8 is compressed. The spring force drives the stop member 9 towards the proximal end, so that the stop member 9 is practically permanently in contact with the adjacent drive member 10, which stays in contact with the drive sleeve 11. The spring 8 thus allows for a certain relative axial movement of the stop member 9, the drive member 10 and the drive sleeve 11 to facilitate relative rotations involving a sliding motion along the ramps 23, 24.

Figure 8:
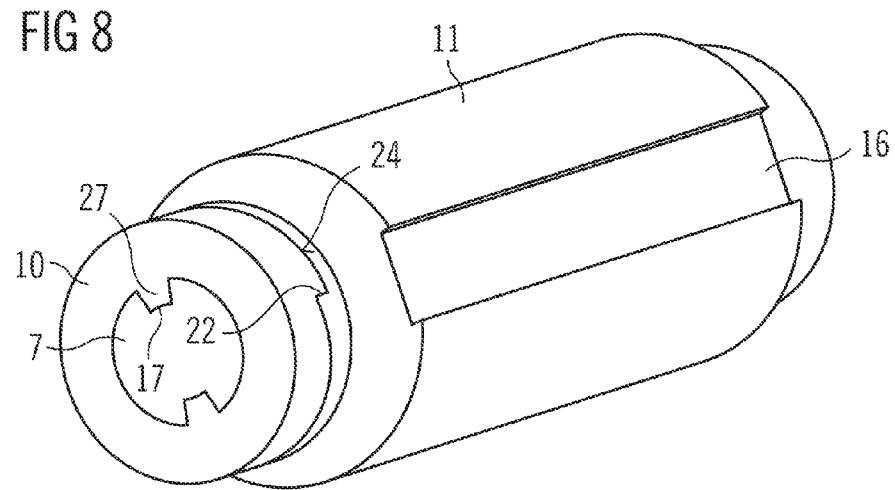
FIG. 8 shows a perspective view of a part of an embodiment of the drive mechanism comprising a dose sleeve, a drive sleeve, a drive member, and a piston rod.

FIG. 8 shows how the piston rod 7 may be rotationally coupled to the drive member 10. To this purpose, the piston rod 7 comprises at least one axial groove 17 or engagement track cutting the screw thread of the piston rod 7 in the axial direction, as can be seen from FIG. 3. A protruding element of the drive member 10, in the embodiment of FIG. 8 an axial thread 27, engages the axial groove 17 of the piston rod 7 and thus allows a relative axial movement of the piston rod 7 with respect to the drive member 10 while at the same time coupling the drive member 10 and the piston rod 7 rotationally. FIG. 8 also shows the ratchet 22 coupling the drive member 10 and the drive sleeve 11. In this embodiment, the drive sleeve 11 is 17 provided with the axial groove 16 also shown in FIG. 2. The drive sleeve 11 may instead be provided with a screw thread, for example.

Although the present invention and its advantages have been described in detail, it should be understood that various changes, substitutions and alterations can be made herein without departing from the spirit and scope of the invention as defined by the appended claims.

The invention claimed is:
1. A drive mechanism for a medication delivery device, comprising:
  a body having a proximal end and a distal end,
  a piston rod arranged within the body along an axis of rotation, a drive member arranged within the body, the drive member being rotationally coupled with the piston rod with respect to the axis of rotation, the piston rod configured for both a helical movement and a separate axial movement without rotation with respect to the body, the helical movement of the piston rod comprising a rotation around the axis of rotation and a simultaneous shift along the axis of rotation, the piston rod comprising a guide track, the guide track comprising a helical element and an axial element, and a guide element arranged within the body, the guide element being fixed relatively to the body, wherein the guide element is coupled to the guide track in such a manner as to guide both the helical movement and the separate axial movement without rotation of the piston rod, and wherein, when the guide element is coupled to the helical element and is rotationally fixed relative to the body during medication delivery, the guide element guides the helical movement of the piston rod, and when the same guide element is coupled to the axial element, it guides the axial movement of the piston rod in a distal direction towards the distal end of the body, the axial movement preceding the helical movement.

2. The drive mechanism according to claim 1, wherein the helical element of the piston rod is a screw thread.

3. The drive mechanism according to claim 2, wherein the axial element of the piston rod is an axial groove leading into the screw thread.

4. The drive mechanism according to claim 1, further comprising:
the drive member being rotationally coupled with the piston rod by means of an axial groove of the piston rod, the axial groove having a limit in the direction of the distal end.

5. The drive mechanism according to claim 4, wherein the drive member is arranged in such a manner that it can be shifted towards the distal end, the drive member is coupled with the piston rod by means of an axial thread engaging the axial groove of the piston rod, the drive member shifts the piston rod towards the distal end when the drive member is shifted towards the distal end while the axial thread is in contact with the limit of the axial groove and the guide element is coupled to the axial element of the piston rod.

6. The drive mechanism according to claim 5, wherein the piston rod is provided to be shifted towards the distal end by the drive member in a priming step.

7. The drive mechanism according to claim 1, further comprising:
a dose sleeve being coupled with the piston rod in such a manner as to allow the piston rod to be shifted towards the distal end by means of the dose sleeve.

8. The drive mechanism according to claim 7, wherein the piston rod is shifted towards the distal end by means of the dose sleeve while the guide element is coupled to the axial element of the piston rod.

9. The drive mechanism according to claim 8, wherein the piston rod is provided to be shifted towards the distal end by the dose sleeve in a priming step.

10. A medication delivery device comprising the drive mechanism according to claim 1, further comprising:
a receptacle at the distal end within the body, and
a piston within the receptacle, the piston being movable along the axis of rotation by means of the piston rod.

11. A medication delivery device according to claim 10, wherein the receptacle is provided for a cartridge, and the piston is inserted in the cartridge.

12. A medication delivery device according to claim 10, wherein a dose is set by a movement of a dose sleeve in the direction to the proximal end, and a medication is delivered by a movement of the dose sleeve in the direction to the distal end.

13. A medication delivery device according to claim 10, wherein the body has a shape of an injection pen.

14. A drive mechanism for a medication delivery device, comprising:
a body having a proximal end and a distal end,
a piston rod having a distal end and arranged within the body along an axis of rotation,
a drive member arranged within the body, the drive member being rotationally coupled with the piston rod with respect to the axis of rotation, the piston rod configured for both a helical movement and a separate axial movement without rotation with respect to the body, the helical movement of the piston rod comprising a rotation around the axis of rotation and a simultaneous shift along the axis of rotation, the piston rod comprising a guide track comprising a helical element and an axial element,
a guide element arranged within the body, the guide element being rotationally fixed relative to the body during medication delivery, wherein the guide element is coupled to the guide track in such a manner as to guide the movement of the piston rod,
a stop member arranged within the body and being rotationally coupled with the body,
a drive sleeve arranged within the body on a side of the drive member facing the proximal end, the drive sleeve being rotatable with respect to the body around the axis of rotation, and
a first gear coupling the drive member and the stop member rotationally when the drive sleeve is rotated in a first sense of rotation around the axis of rotation.

15. The drive mechanism according to claim 14, further comprising:
a spring arranged within the body, the spring exerting a force on the stop member in a proximal direction towards the proximal end,
a second gear coupling the drive member and the drive sleeve rotationally when the drive sleeve is rotated in a second sense of rotation, which is opposite to the first sense of rotation, around the axis of rotation,
a dose sleeve arranged within the body, the dose sleeve being helically movable with respect to the body, the movement comprising a rotation around the axis of rotation and a simultaneous shift along the axis of rotation, and
a coupling between the dose sleeve and the drive sleeve, the coupling producing a rotation of the drive sleeve in the second sense of rotation around the axis of rotation when the dose sleeve is moved towards the distal end.

16. The drive mechanism according to claim 15, wherein the helical movement of the piston rod advances the piston rod towards the distal end when the piston rod is rotated in the second sense of rotation with respect to the body.

17. The drive mechanism of claim 14 where the piston rod moves helically relative to the guide element during dose delivery.

18. A drive mechanism for a medication delivery device, comprising:
a body having a proximal end and a distal end,
a piston rod arranged within the body along an axis of rotation, the piston rod having a distal end, a drive member arranged within the body, the drive member being rotationally coupled with the piston rod with respect to the axis of rotation, the piston rod being helically movable with respect to the body, the helical movement of the piston rod comprising a rotation around the axis of rotation and a simultaneous shift along the axis of rotation, the piston rod comprising a guide track, the guide track comprising a helical element and an axial element, and a guide element arranged within the body, the guide element being fixed relatively to the body, wherein the guide element is rotationally fixed relative to the body during medication delivery and is coupled to the guide track in such a manner as to cause first the axial movement without the helical movement followed by the helical movement of the piston rod, and wherein, the helical element of the guide track is arranged further away from the distal end than the axial element of the guide track.

* * * * *